United States Patent [19]
Ramadan

[11] Patent Number: 6,022,335
[45] Date of Patent: Feb. 8, 2000

[54] IMPLANTABLE HEMODIALYSIS TRIPLE PORT ASSEMBLY

[76] Inventor: Hossein Ramadan, 168 Hidden Ridge Dr., Syosset, N.Y. 11791

[21] Appl. No.: 09/108,815

[22] Filed: Jul. 1, 1998

[51] Int. Cl.$^7$ .................................................. A61M 11/00
[52] U.S. Cl. .................. 604/93; 604/4; 604/175
[58] Field of Search .............................. 604/93, 174, 175, 604/82, 86, 4

[56] References Cited

U.S. PATENT DOCUMENTS

| 3,756,243 | 9/1973 | Schulte . | |
|---|---|---|---|
| 4,557,722 | 12/1985 | Harris | 604/9 |
| 5,085,644 | 2/1992 | Watson et al. | 604/153 |
| 5,102,389 | 4/1992 | Hauser | 604/93 |

*Primary Examiner*—Corrine McDermott
*Attorney, Agent, or Firm*—Michael I Kroll

[57] ABSTRACT

An implantable dialysis connection assembly for connecting first and second catheters positioned with a vein to first and second terminals of a dialysis machine. The assembly includes a housing having first, second and third recesses extending into a face side thereof. A first port is positioned within the first recess for receiving the first terminal and retaining an end of the first terminal within the first recess. A second port is positioned within the second recess for receiving the second terminal and retaining an end of the second terminal within the second recess. A third port is positioned within the third recess for connecting to a supply of heparin for deposit within the third recess. The third port is connected to the first port for supplying heparin thereto by a first conduit and the third port is connected to the second port for supplying heparin thereto by a second conduit. First and second connection devices connect the first and second ports to the first and second conduits, respectively. In operation, the first terminal causes blood to be removed from the vein through the first catheter and first recess for delivery to and detoxification by the dialysis machine and the second terminal causes detoxified blood to be returned to the vein through the second recess and second catheter, said heparin being supplied to said first and second recesses during dialysis for preventing the blood passing through said first and second recesses from clotting and thereby clogging the first and second terminals.

19 Claims, 9 Drawing Sheets

IMPLANTABLE HEMODIALYSIS TRIPLE PORT ASSEMBLY

BACKGROUND OF THE INVENTION

1. Field of the Invention

The present invention relates generally to dialysis access, and can be used as an alternative, to A-V Fistula, A-V Graft and external catheters and, more specifically, to an implantable hemodialysis triple port assembly which will provide a cosmetically appealing apparatus for long term dialysis patients, a fault tolerant apparatus for health care professionals who sometimes fail to flush the catheter with a heparinized solution after each use; and relieve overburdened doctors and hospitals from repeated surgery required for creation of arteriovenous fistulas, arteriovenous grafts and the treatment of their complications, such as clotting, usually requiring one to three hospitalizations per patient per year to either declot the graft or fistula or create a new one. The implantable hemodialysis triple port assembly will also eliminate the need for an external dialysis catheter while preventing problems such as frequent clotting, infection and inconvenience to the patient associated therewith.

2. Description of the Prior Art

Hemodialysis acts to purify the blood by passing it through a dialysis machine at a rate of 300–500 cc per minute. In order to perform this procedure two (2) large needles (at least 16G) are required for piercing a vein or graft (called angio-access) of sufficient size to provide an appropriate flow of blood. One needle will act to withdraw blood from the patient for delivery to the dialysis machine and the other needle will act to return the purified blood from the dialysis machine to the patient. Each hemodialysis session usually lasts 2–4 hours and must be performed three times a week over the course of the patient's life.

The veins of the arms are not large enough to accommodate the withdrawal of 300–500 cc of blood per minute extracted by the dialysis machines. Therefore, the veins in the arm must be enlarged by creating a fistula between an artery and vein (A-V Fistula). This may be performed in only a small percentage of dialysis patients due to the small or fibrotic veins associated with renal failure patients making them unsuitable for creation of a fistula. Furthermore, when the fistula has been successfully created a period of 4–8 weeks is needed in order for the fistula to mature before it can be used for dialysis.

A second option for angio access is creating an arterial-venous graft. This is performed using a synthetic tube, requires a patient to remain in the hospital for several days and takes 1–3 weeks before the graft can be used. There is also a high rate of complication due to clotting, infection and arm swelling associated with this procedure. Thus, declotting and frequent replacement of the graft are normally required.

The third option is implanting an external temporary catheter to be used until the A-V Fistula or shunt is ready for use. This procedure also has pitfalls such as inconvenience to the patient as it remains outside the skin, frequent infection and the need for the catheter to be replaced.

Numerous types of devices for aiding in dialysis treatment have been provided in the prior art. For example, U.S. Pat. Nos. 4,846,806; 4,892,518; 4,950,259 and 5,037,385 all are illustrative of such prior art. While these units may be suitable for the particular purpose to which they address, they would not be as suitable for the purposes of the present invention as heretofore described.

U.S. Pat. No. 4,846,806

Inventor: Bruce D. Wigness et al.

Issued: Jul. 11, 1989

An implantable intravascular access system, including an implantable, catheter obturator controller manifold for use with an implantable intravascular catheter. The catheter includes a lumen, having an expanded state and a normal state, an obturator, and an obturator plenum having an inflated state and a contracted state. T he lumen can be closed or opened by hydraulically actuating the expansion or contraction of the obturator plenum when the lumen is in the normal state. When the obturator plenum is expanded to its inflated state, the obturator substantially blocks the lumen such that substantially no fluid can pass through the lumen when the lumen is in its normal state. The manifold comprises a housing, a receiving mechanism for receiving the catheter, an actuating mechanism for hydraulically actuating the expansion or contraction of the plenum, and a first entry mechanism for entering the housing.

U.S. Pat. No. 4,892,518

Inventor: James R. Cupp et al.

Issued: Jan. 9, 1990

Hemodialysis port assembly including a port and a catheter assembly. The port includes an inlet septum subtended by an inlet plenum and an outlet septum subtended by an outlet plenum. The catheter assembly includes an inlet channel connected to the inlet plenum and an outlet channel connected to the outlet plenum. The port and catheter assembly are completely implanted in the chest of a patient with the port subcutaneous and the end of the catheter assembly remote from the port injected into the subclavian vein. The blood flow in this vein is in the direction away from the end of the catheter assembly. Near this remote end the catheter assembly or the inlet channel terminates in an outlet valve. Each of these valves is essentially a flapper on which the blood is incident in a generally perpendicular direction so that its flow is substantially unimpeded. The outlet valve is spaced a small but effective distance from the inlet valve in the downstream direction of the flow to toxified blood through the outlet channel. In practice of this invention, the detoxified blood from an artificial kidney is supplied to the vein through a hypodermic needle which penetrates the inlet septum, the inlet plenum, the inlet channel and the inlet valve and toxified blood is supplied from the vein to the artificial kidney through the outlet valve, the outlet channel, the outlet plenum and an outlet needle which penetrates the outlet septum. The spacing of the outlet valve from the inlet valve suppresses short circuit flow of detoxified blood from the inlet branch to the outlet branch.

U.S. Pat. No. 4,950,259

Inventor: Denis F. Geary et al.

Issued: Aug. 21, 1990

A double lumen flexible catheter for peritoneal dialysis comprises a double lumen structure with inner and outer tubes. The outer tube has a plurality of openings the inner tube being stretched in tension to prevent kinking of the catheter. The inner tube has a single outlet at the free end of the catheter. The tubing for the catheter is sufficiently flexible to permit the catheter to lie loosely and freely in the body cavity. Treatment fluids are delivered to the peritoneal cavity through the inner tube and removed via the outer tube.

U.S. Pat. No. 5,037,385

Inventor: Paul O'Byrne

Issued: Aug. 6, 1991

A wholly implantable continuous ambulatory peritoneal dialysis system comprises a first part including tubing for location as an access catheter affording a flowpath for dialyzing solution from a subcutaneous portal, accessible by percutaneous needle, to the peritoneal cavity, and a second part including a pump and a further tubing serially interconnectable for location as a shunt affording a flowpath for the solution, following dialysis, from the cavity to the bladder, the pump being operable under control by the patient to effect the shunt flow.

SUMMARY OF THE PRESENT INVENTION

The present invention relates generally to devices for connecting a dialysis machine to a patient in need of hemodialysis and, more specifically, to an implantable device, placed under the subcutaneous tissue in the left or right subclavicular area and connected to two catheters inserted percutaneously into the superior vena cava via subclavian or internal jugular veins. The implantable device may be connected to a dialysis machine by insertion of two 16G anti-coring needles into the ports of the implantable device and connecting the anti-coring needles to the dialysis machine.

A primary object of the present invention is to provide an implantable assembly for connecting a dialysis machine to a patient that will overcome the shortcomings of prior art devices.

Another object of the present invention is to provide an implantable assembly for connecting a dialysis machine to a patient which is cosmetically appealing to the user while allowing the user to assume a normal life style between dialysis treatments without the risk of epidermal infection normally associated with tubes providing external access to implanted catheters.

A further object of the present invention is to provide an implantable assembly for connecting a dialysis machine to a patient including identical arterial and venous ports which are easily locatable and discernible by application of light pressure to the skin with a hand.

A yet further object of the present invention is to provide an implantable assembly for connecting a dialysis machine to a patient wherein the arterial and venous ports are accessible using right angle anti-coring needles attached to the dialysis machine.

A still further object of the present invention is to provide an implantable assembly for connecting a dialysis machine to a patient including a third heparin port connected to both the arterial and venous ports for storing a supply of heparin therein and supplying the heparin to the arterial and venous ports.

A further object of the present invention is to provide an implantable assembly for connecting a dialysis machine to a patient wherein the arterial and venous ports have a surface area of a size able to provide a large number of insertion points thereby allowing an area time to heal after puncture with the needle.

A further object of the present invention is to provide an implantable assembly for connecting a dialysis machine to a patient wherein the heparin is supplied to the arterial and venous ports by osmosis and acts as an anti-clotting mechanism.

Another object of the present invention is to provide an implantable assembly for connecting a dialysis machine to a patient wherein the arterial, venous and heparin ports are formed from a self sealing material such as rubberized silicone for preventing the release of any fluids therefrom except through the needle inserted therein.

A still further object of the present invention is to provide an implantable assembly for connecting a dialysis machine to a patient wherein each of the arterial, venous and heparin ports are lined with a suitably dense material for preventing the needle from piercing the walls of the port.

Another object of the present invention is to provide an implantable assembly for connecting a dialysis machine to a patient that is simple and easy to use.

A still further object of the present invention is to provide an implantable assembly for connecting a dialysis machine to a patient that is economical in cost to manufacture.

Additional objects of the present invention will appear as the description proceeds.

An implantable dialysis connection assembly for connecting first and second catheters positioned with a vein to first and second terminals of a dialysis machine is disclosed by the present invention. The assembly includes a housing having first, second and third recesses extending into a face side thereof. A first port is positioned within the first recess for receiving the first terminal and retaining an end of the first terminal within the first recess. A second port is positioned within the second recess for receiving the second terminal and retaining an end of the second terminal within the second recess. A third port is positioned within the third recess for connecting to a supply of heparin for deposit within the third recess. The third port is connected to the first port for supplying heparin thereto by a first conduit and the third port is connected to the second port for supplying heparin thereto by a second conduit. First and second connection devices connect the first and second ports to the first and second conduits, respectively. In operation, the first terminal causes blood to be removed from the vein through the first catheter and first recess for delivery to and detoxification by the dialysis machine and the second terminal causes detoxified blood to be returned to the vein through the second recess and second catheter, said heparin being supplied to said first and second recesses during and after dialysis for preventing the blood passing through said first and second recesses from clotting and thereby clogging the first and second terminals.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

DESCRIPTION OF THE REFERENCED NUMERALS

Turning now descriptively to the drawings, in which similar reference characters denote similar elements throughout the several views, the Figures illustrate the implantable assembly for connecting a dialysis machine to a patient of the present invention. With regard to the reference numerals used, the following numbering is used throughout the various drawing figures.

10 implantable assembly for connecting a dialysis machine to a patient of the present invention
12 patient
13 housing
14 face side of housing
15 first port
16 second port
18 third port
20 first conduit between first port and third port
22 second conduit between second port and third port
24 first passageway for connecting first port to a first catheter
26 first catheter
28 second passageway for connecting second port to a second catheter
30 second catheter
32 superior vena cava
34 heart
36 first securing device
38 second securing device
40 first connection port
42 second connection port
44 base section of first connection port
46 side wall of housing
48 connection section of first connection port
50 base section of second connection port
52 connection section of second connection port
54 first recess for receiving the first port
56 second recess for receiving the second port
58 third recess for receiving the third port
60 side wall of first recess
62 side wall of second recess
64 side wall of third recess
66 entrance to interior of first recess
68 entrance to interior of second recess
70 first sealing device
72 second sealing device
74 third sealing device
76 first right angle anti-coring needle
78 second right angle anti-coring needle
80 third right angle anti-coring needle
82 first end of first right angle anti-coring needle
84 second end of first right angle anti-coring needle
86 opening of first right angle anti-coring needle
88 first end of second right angle anti-coring needle
90 second end of second right angle anti-coring needle
92 opening of second right angle anti-coring needle
94 first end of third right angle anti-coring needle
96 second end of third right angle anti-coring needle
98 opening of third right angle anti-coring needle
100 recess in side wall of housing
102 protrusion extending from port and through recess
104 thread spiraling around protrusion
106 thread spiraling around inner side of base section of connection port
108 side of protrusion
110 outlet catheter
112 compression sleeve
114 mid section of connection port

DETAILED DESCRIPTION OF THE PREFERRED EMBODIMENT

Turning now descriptively to the drawings, in which similar reference characters denote similar elements throughout the several views, FIGS. 1 through 9 illustrate the implantable dialysis connection assembly of the present invention indicated generally by the numeral 10.

Figure 1:
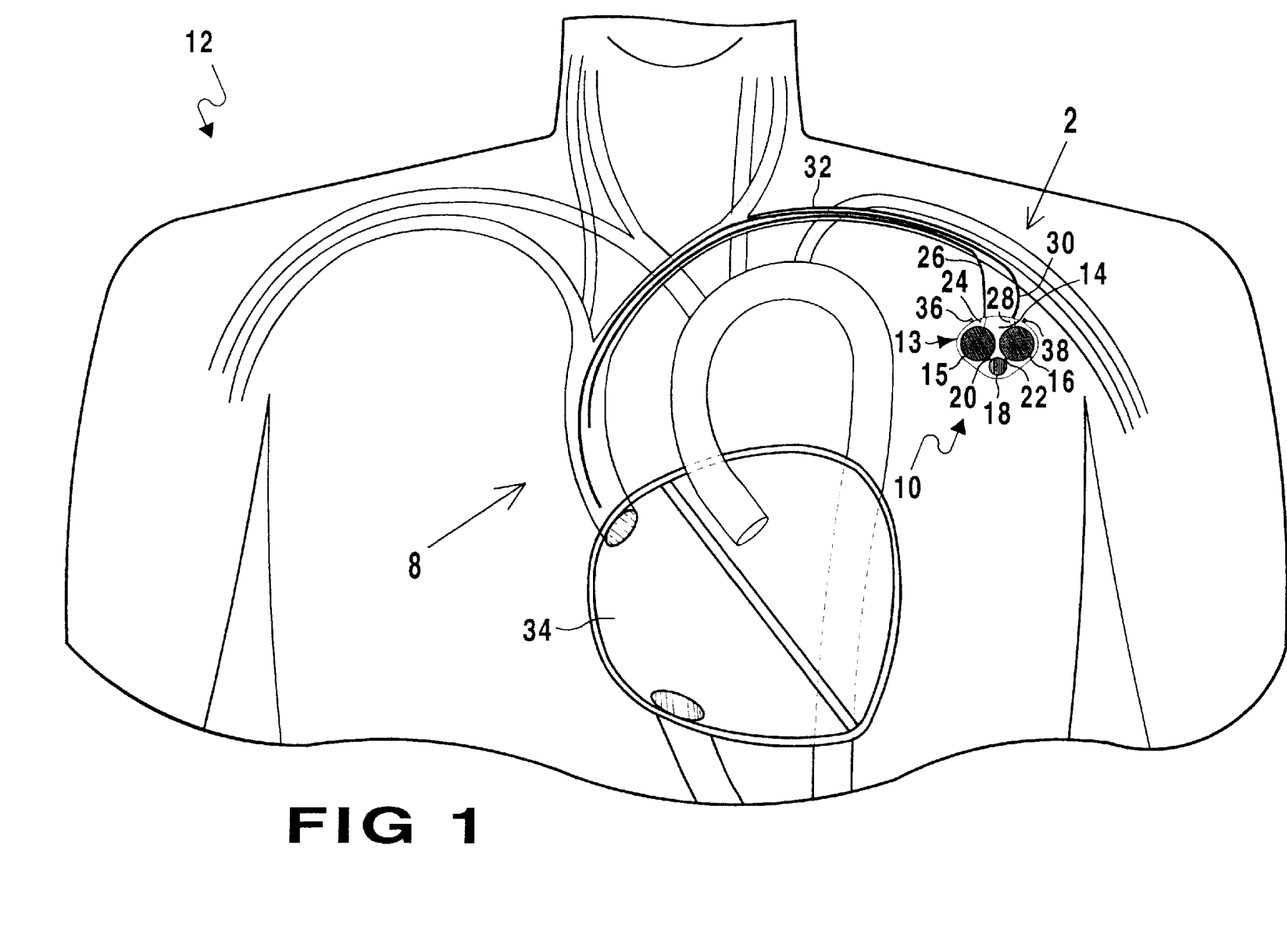
FIG. 1 is a front perspective view of the implantable assembly for connecting a dialysis machine to a patient of the present invention positioned under subcutaneous tissue in the left subclavicular area of a patient and connected to two catheters inserted percutaneously into the superior vena cava via the subclavian veins.

The implantable dialysis connection assembly 10 is illustrated in FIG. 1 positioned below subcutaneous tissue in a left subclavicular area of a patient 12. The implantable dialysis connection assembly 10 includes a housing 13. Held within the housing 13 and accessible through a face side 14 thereof is a first port 15 for receiving a first needle from a dialysis machine, a second port 16 for receiving a second needle from the dialysis machine, and a third port 18 for receiving and storing heparin therein. Heparin is an anti-clotting agent which prevents the clotting of blood. The third port 18 is connected to the first port 15 by a first conduit 20 and is connected to the second port 16 by a second conduit 22. The third port 18 supplies the heparin supplied via the third needle and stored therein to both the first and second ports 15 and 16 via the first and second conduits 20 and 22, respectively. The heparin prevents blood passing through the first and second ports 15 and 16 from clotting and thereby clogging the ports 15 and 16.

Extending from the first port 15 is a first passageway 24 for connection to a first catheter 26. A second passageway 28 extends from the second port 16 for connection with a second catheter 30. The first and second catheters 26 and 30, respectively, are both positioned in a vein 32 supplying blood to the heart 34. Preferably, the first and second catheters 26 and 30, respectively, are positioned to extend into the superior vena cava of the patient 12. The superior vena cava supplies oxygen depleted blood from the upper extremities to the heart 34. One of the first and second catheters 26 and 30 will remove blood from the vein 32, supplying the blood to a dialysis machine connected to one of the first and second ports 15 and 16, respectively, for detoxification. The other of the first and second catheters 26 and 30, respectively, will return the detoxified blood to the vein 32 through the other of the first and second ports 15 and 16, respectively, for supplying the blood to the heart for pumping around the body of the patient.

The implantable dialysis connection assembly 10 is secured in position by first and second securing devices 36 and 38, respectively. The first and second securing devices 36 and 38 are fastened in position below subcutaneous tissue in a left subclavicular area of a patient 12 by either sutures or staples and thereby is prevented from moving.

Figure 2:
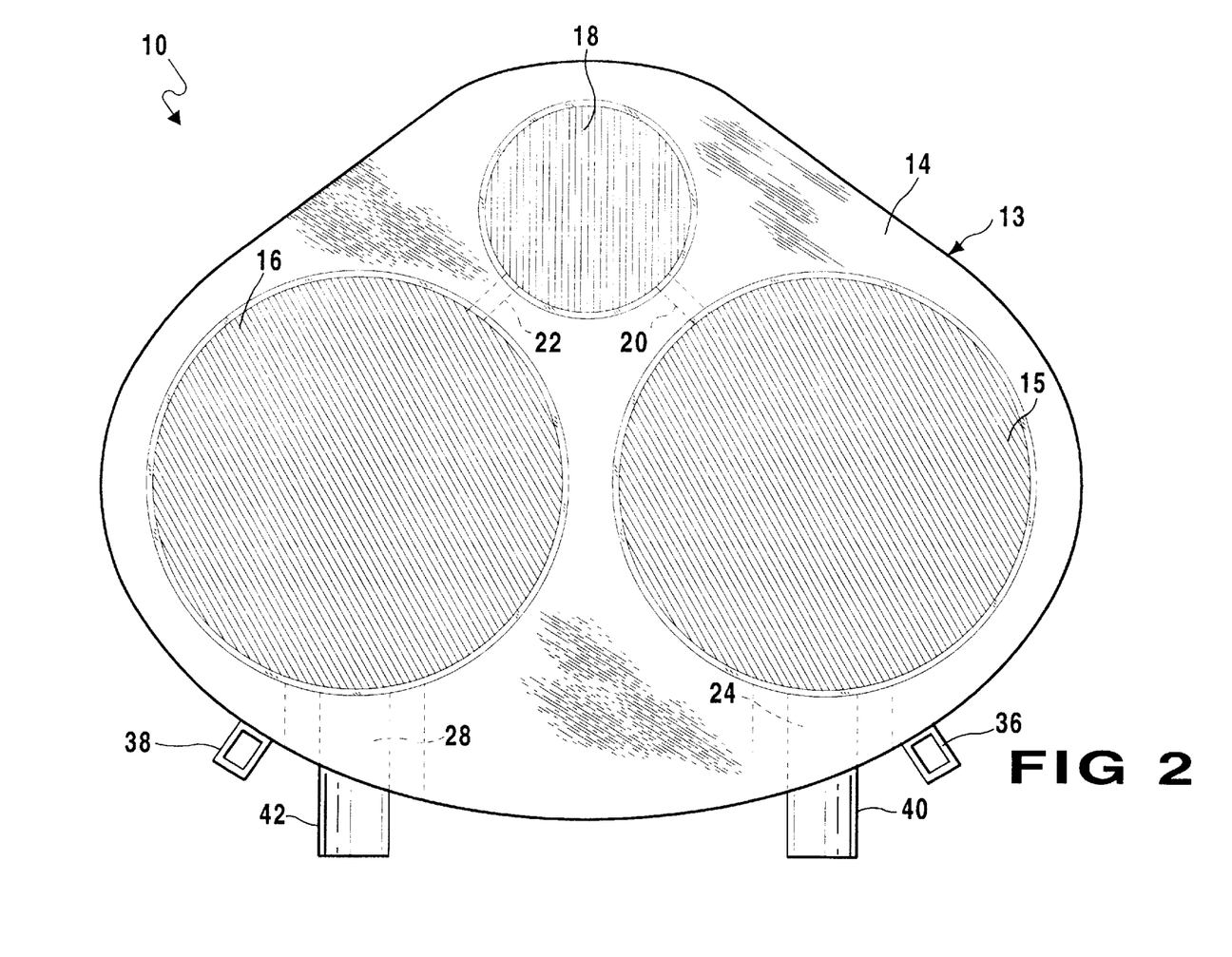
FIG. 2 is an enlarged top view of the implantable assembly for connecting a dialysis machine to a patient of the present invention.

The face side 14 of the housing 13 of the implantable dialysis connection assembly 10 is illustrated in FIG. 2. From this view the first, second and third ports 15, 16 and 18 can be clearly seen. The first and second conduits 20 and 22, respectively, are illustrated in dashed lines. The first and second passageways 24 and 28 are also illustrated in dashed lines. Extending from the first passageway 24 is a first connection port 40 for connection to the first catheter 26 and extending from the second passageway 28 is a second connection port 42 for connection to the second catheter 30. The first and second ports 15 and 16 may be used as either an arterial (inflow) port or a venous (outflow) port interchangeably dependent upon the terminal connections to the dialysis machine. The first and second conduits 20 and 22, respectively, provide a supply of heparin from the third port 18 to the first and second ports 15 and 16, respectively, for preventing blood flowing therethrough from clotting and thereby clogging the first and second catheters.

The first and second securing devices 36 and 38 extend from the housing 13 adjacent the first and second connection ports 40 and 42 for securing the implantable dialysis connection assembly 10 in position. By securing the implantable dialysis connection assembly 10 at these locations, the connection between the first and second catheters 26 and 30 and the first and second connection ports 40 and 42 are held secure and thus the possibility of the connection therebetween being ruptured or broken is minimized.

Figure 3:
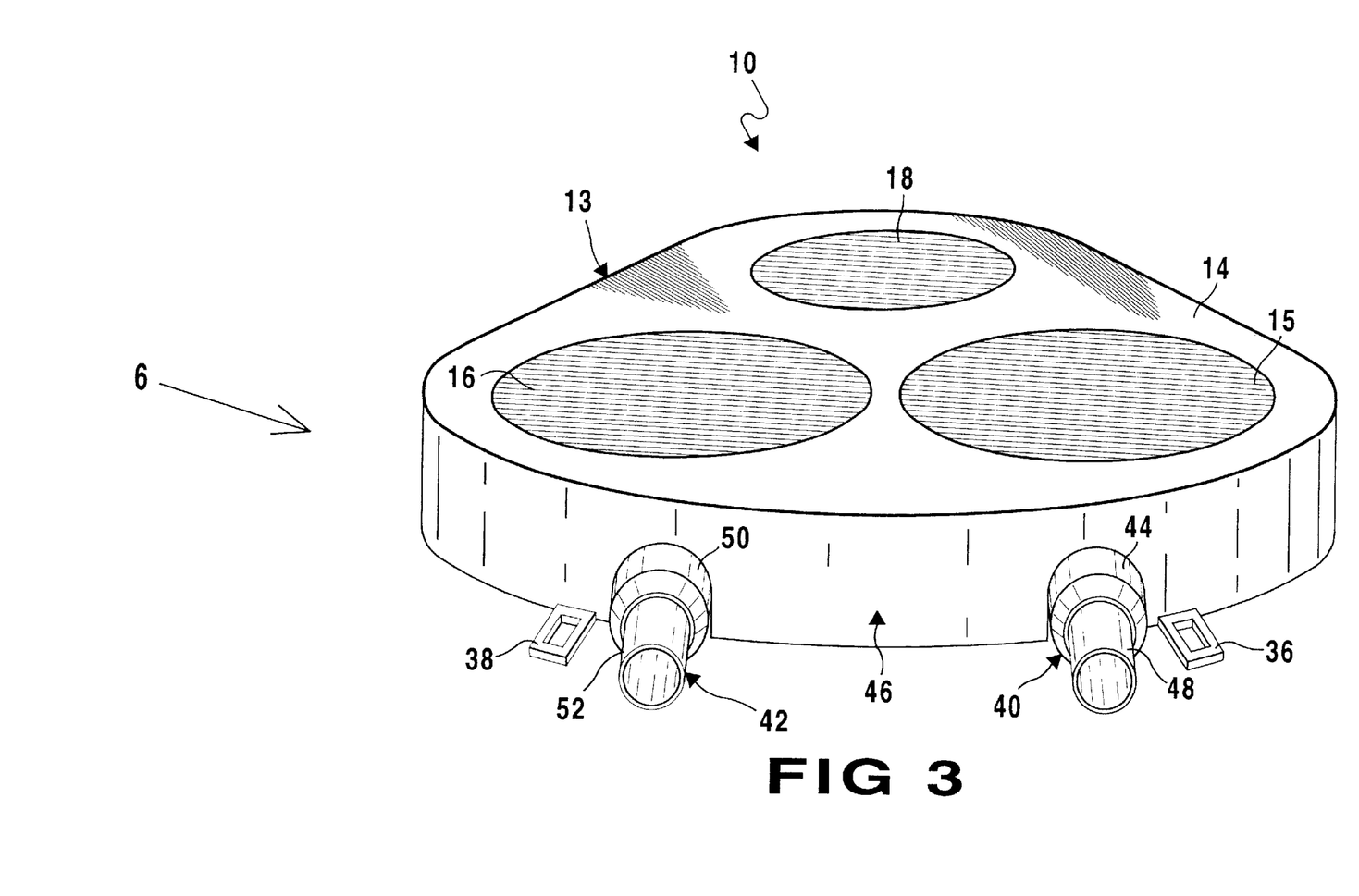
FIG. 3 is a side perspective view of the implantable assembly for connecting a dialysis machine to a patient of the present invention.

A side view of the implantable dialysis connection assembly 10 is illustrated in FIG. 3. From this view, the first and second connection ports 42 and 44 are clearly seen. The first connection port 40 includes a hollow base section 44 connected to a side wall 46 of the housing 13. Extending from the base section 44 is a connection section 48 for connecting with the first catheter 26. The connection section 48 is hollow and includes an inner side having a circumference substantially equal to an inner circumference of the hollow base section 44. The first catheter 26 has an outer circumference substantially equal to the circumference of the connection section 48 for forming a tight seal therebetween. The second connection port 42 includes a hollow base section 50 connected to the side wall 46 of the housing 13. Extending from the base section 50 is a connection section 52 for connection to the second catheter 30. The connection section 52 is hollow and includes an inner side having a circumference substantially equal to an inner circumference of the hollow base section 50. The second catheter 30 has an outer circumference substantially equal to the circumference of the connection section 52 for forming a tight seal therebetween.

While a preferred structure and device for connecting the implantable dialysis connection assembly 10 to a catheter are shown and described herein, those of ordinary skill in the art who have read the description will appreciate that there are numerous other devices for connecting the implantable dialysis connection assembly 10 to a catheter and, therefore, as used herein the phrase "means for connecting the implantable dialysis connection assembly to a catheter" should be construed as including all such devices as long as they achieve the desired result of connecting the implantable dialysis connection assembly 10 to a catheter, and, therefore, that all such equivalent mechanisms and combinations are to be considered as equivalents to the ones described herein.

Figure 4:
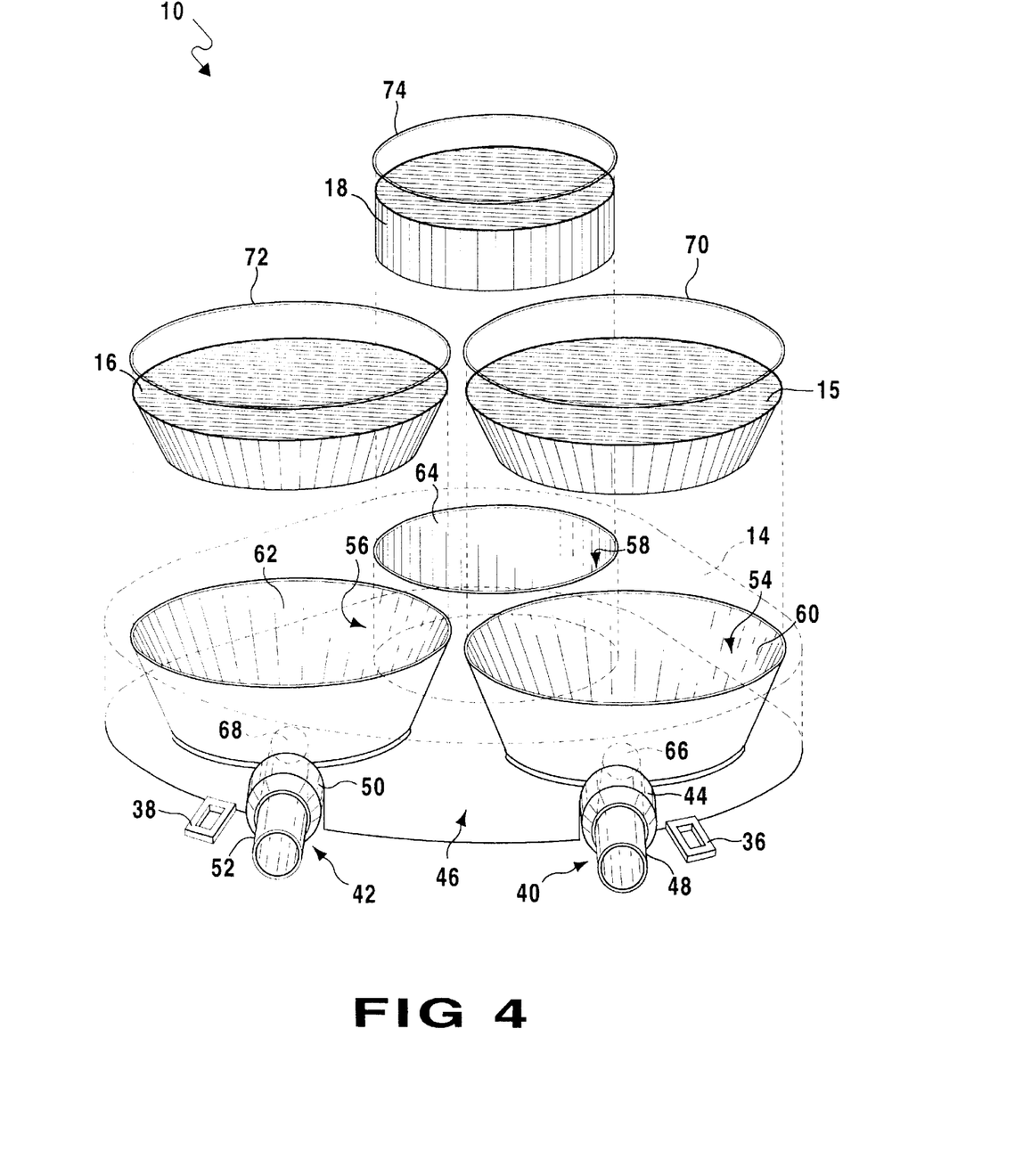
FIG. 4 is a exploded top perspective view of the implantable assembly for connecting a dialysis machine to a patient of the present invention.

An exploded view of the implantable dialysis connection assembly 10 including the first, second and third ports removed therefrom is illustrated in FIG. 4. As can be seen from this figure, the housing 13 includes a first recess 54 for receiving the first port 15, a second recess 56 for receiving the second port 16 and a third recess 58 for receiving the third port 18. The first recess 54 preferably has a slanted side wall 60 and the second recess 56 also preferably has a slanted side wall 62. The side wall 64 of the third recess 58 preferably extends perpendicular to the face side 14 of the housing 13. The side wall 60 of the first recess 54 includes an entrance 66 connecting an interior of the first recess 54 to the hollow base section 44 of the first connection device 40 thereby allowing communication between the first port 15 and the first catheter 26. The side wall 62 of the second recess 56 includes an entrance 68 connecting an interior of the second recess 56 to the hollow base section 50 of the second connection device 42 thereby allowing communication between the second port 16 and the second catheter 30.

The first, second and third ports 15, 16 and 18, respectively, are preferably formed of a rubberized silicone material able to seal any septum created by passage of a needle therethrough as occurs when needles are inserted into the first and second ports for connecting the implantable dialysis connection assembly 10 to a dialysis machine. The first, second and third ports 15, 16 and 18, respectively, may also be formed of any one of a sponge material, foam, a rubberized material, any self sealing material and any combination thereof. The first and second ports 15 and 16, respectively, are thus able to absorb the heparin supplied by the third port and any blood passing therethrough. The blood and heparin are combined in the first and second ports and allowed to pass therethrough either to a needle positioned therein connected to the dialysis machine or to the catheter and vein from the needle connected to the dialysis machine dependent upon the terminal connections to the dialysis machine. The third recess 58 stores heparin below the third port for providing a regulated supply to the first and second ports. The first port 15 is retained within the first recess 54 by a first sealing device 70, the second port 16 is retained in the second recess 56 by a second sealing device 72 and the third port 18 is retained in the third recess 58 by a third sealing device 74.

Figure 5:
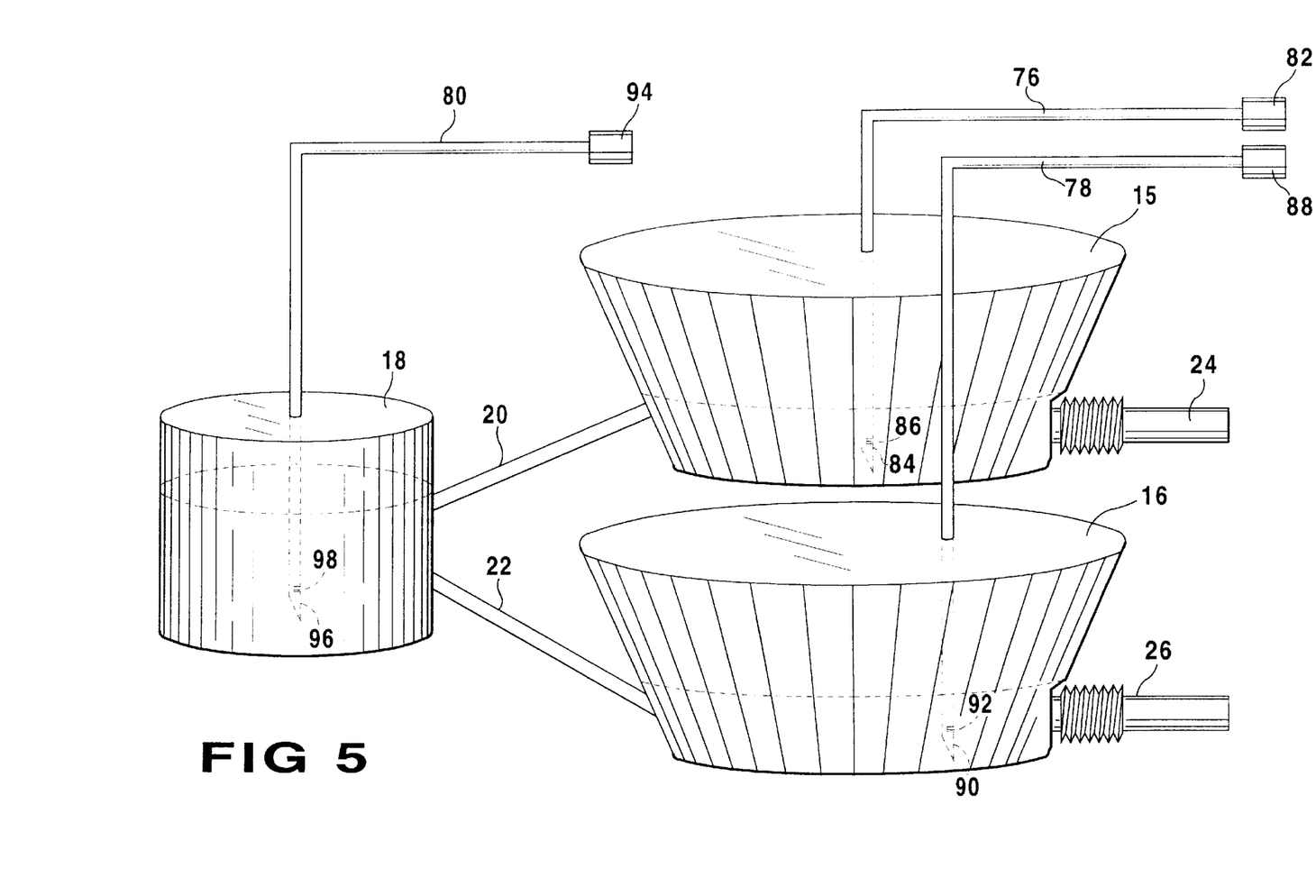
FIG. 5 is a side perspective view of the ports of the implantable assembly for connecting a dialysis machine to a patient of the present invention removed from the housing and including right angle anti-coring needles extending therefrom.

The first, second and third ports 15, 16 and 18, respectively, are illustrated removed from the housing 13 in FIG. 5. The first port 15 includes a first right angle anti-coring needle 76 removably extending therefrom. The second port 16 includes a second right angle anti-coring needle 78 removably extending therefrom. The third port 18 includes a third right angle anti-coring needle 80 removably extending therefrom. The first right angle anti-coring needle 76 includes a first end 82 for connection to a first terminal of a dialysis machine and a second pointed end 84 for extending into the first port 15. The first right angle anti-coring needle 76 is hollow and includes an opening 86 for the passage of blood therethrough. The second right angle anti-coring needle 78 includes a first end 88 for connection to a second terminal of a dialysis machine and a second pointed end 90 for extending into the second port 16. The second right angle anti-coring needle 78 is hollow and includes an opening 92 for the passage of blood therethrough. The third right angle anti-coring needle 80 includes a first end 94 for connection to a supply of heparin and a second pointed end 96 for extending into the third port 18. The third right angle anti-coring needle 80 is hollow and includes an opening 98 for the passage of heparin therethrough. The heparin delivered to and stored in the third port 18 is delivered to the first port 15 through the first conduit 20 and to the second port 16 via the second conduit 22. The blood and heparin within the first recess 54 is passed between the first right angle anti-coring needle 76 and the first conduit 20 via the first connection port 24. The blood and heparin within the second recess 56 is passed between the second right angle anti-coring needle 78 and the second conduit via the second connection port 26.

Figure 6:
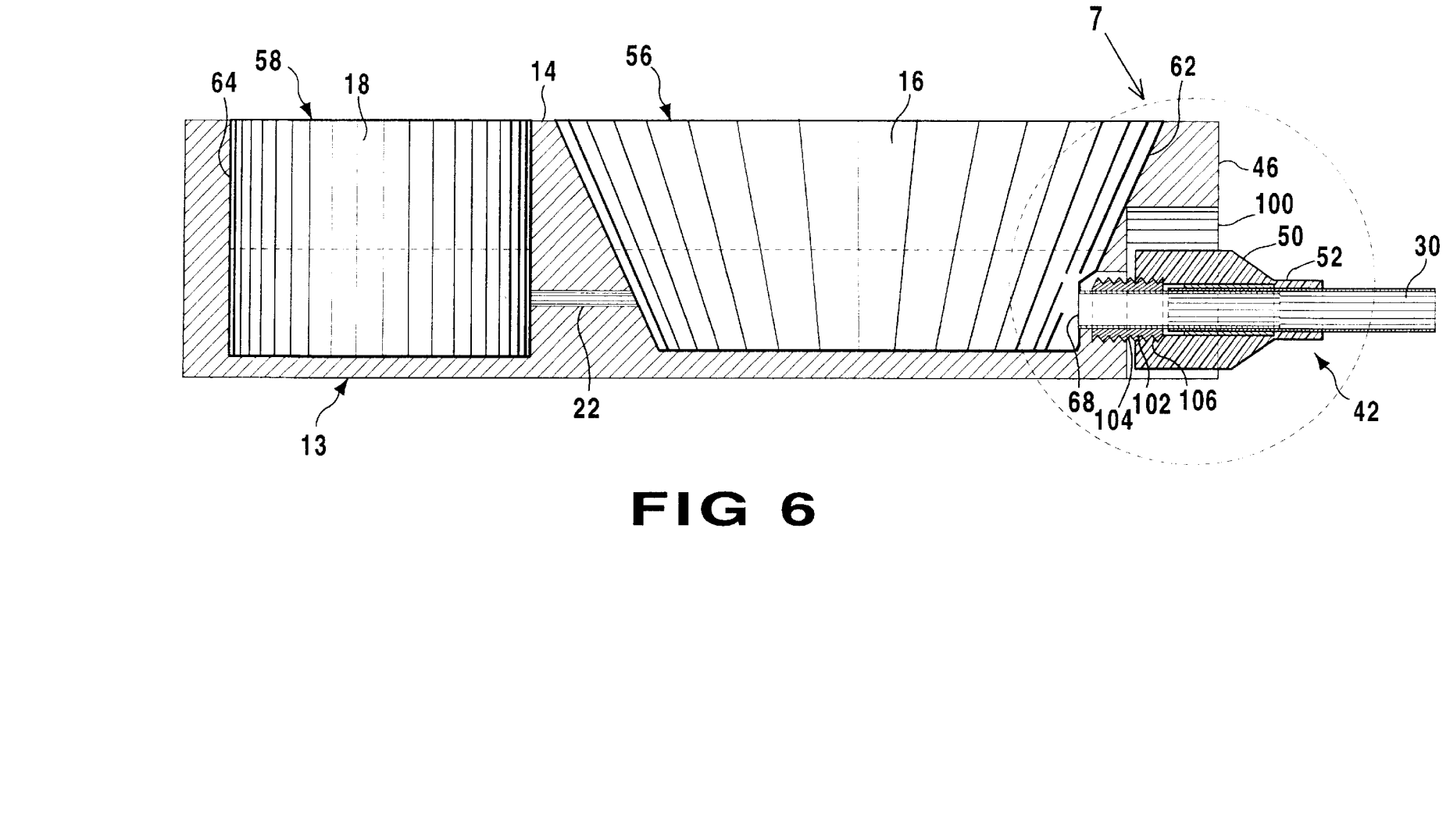
FIG. 6 is a side cross-sectional view of the implantable assembly for connecting a dialysis machine to a patient of the present invention.
Figure 7:
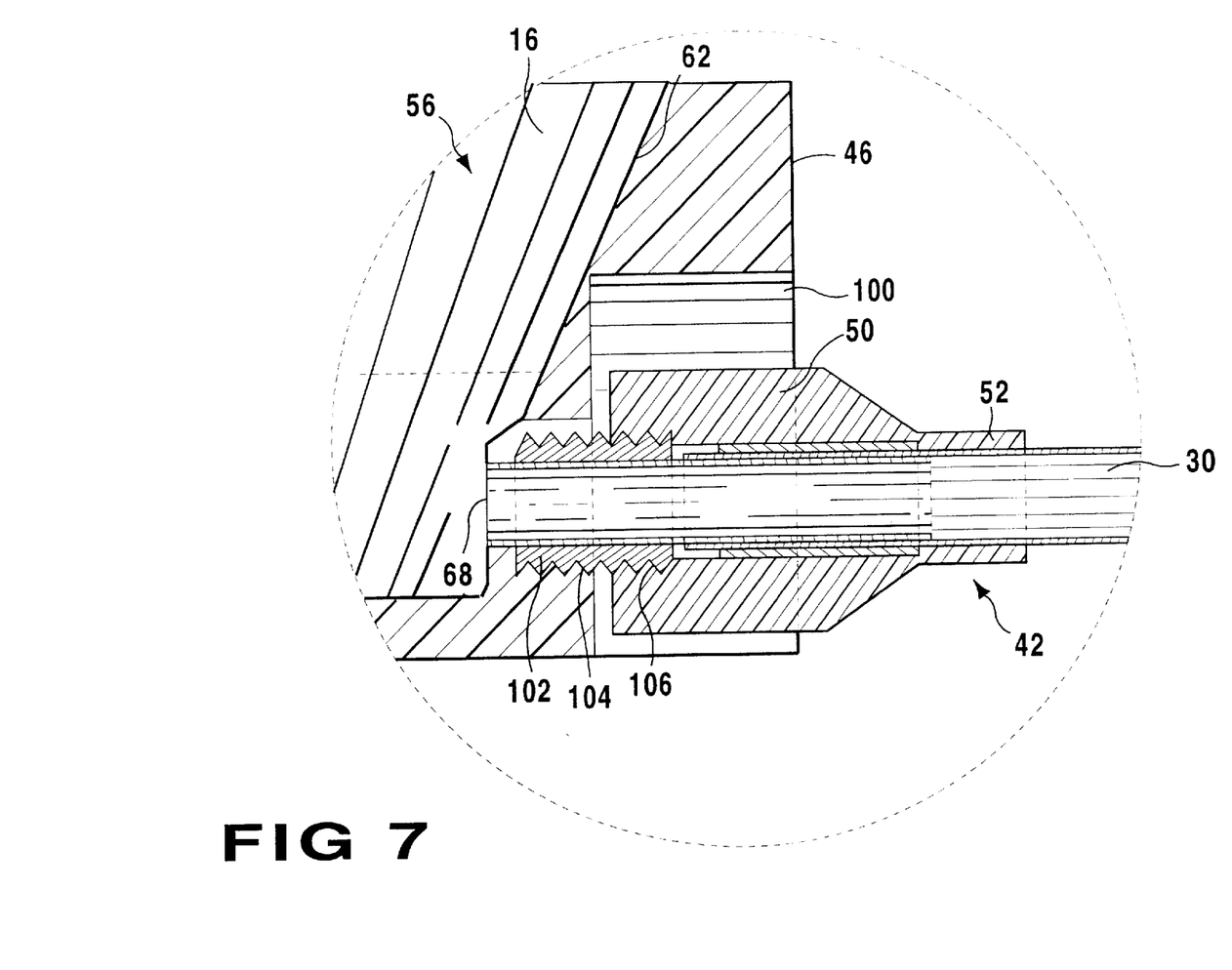
FIG. 7 is an exploded side view of the catheter connection port of the implantable assembly for connecting a dialysis machine to a patient of the present invention taken within the circle labeled 7 in FIG. 6.

A side cross-sectional view of the implantable dialysis connection assembly 10 is illustrated in FIG. 6. A preferred connection between the second port 16 and the second catheter 30 via the second connection device 42 is clearly seen by this figure. The description and illustration of the connection between the second port 16 and the second catheter 30 is for purposes of illustration only. The first port 15 and first catheter 26 may be connected in the same manner. The base section 50 of the second connection port 42 is secured within a recess 100 extending into the side wall 46 of the housing 13. A protrusion 102 including a thread 104 spiraling therearound extends from the recess 100 and engages a thread 106 spiraling around a portion of an inner side of the base section 50 thereby securing the base section to the protrusion 102 and thus to the housing 13. The securing section 52 of the connection port 42 extends from the housing 13 and receives the catheter 30 therein. The catheter 30 is caused to extend completely through the connection port 42 and sit flush against the entrance 68 to the second port 16. The catheter 30 is thus securely held within the connection port 42 for retaining its contact with the second port 16. The connection between the second and third ports 16 and 18, respectively, via the second conduit 22 is also depicted in this figure. An enlarged view of the connection device 42 illustrated in FIG. 6 and contained within the circle labeled 7 is also illustrated in FIG. 7.

While a preferred structure and device for connecting the catheter to its respective port are shown and described herein, those of ordinary skill in the art who have read the description will appreciate that there are numerous other devices for catheter to its respective port and, therefore, as used herein the phrase "means for connecting the catheter to said port" should be construed as including all such devices as long as they achieve the desired result of connecting the catheter to its respective port, and, therefore, that all such equivalent mechanisms and combinations are to be considered as equivalents to the ones described herein.

Figure 8:
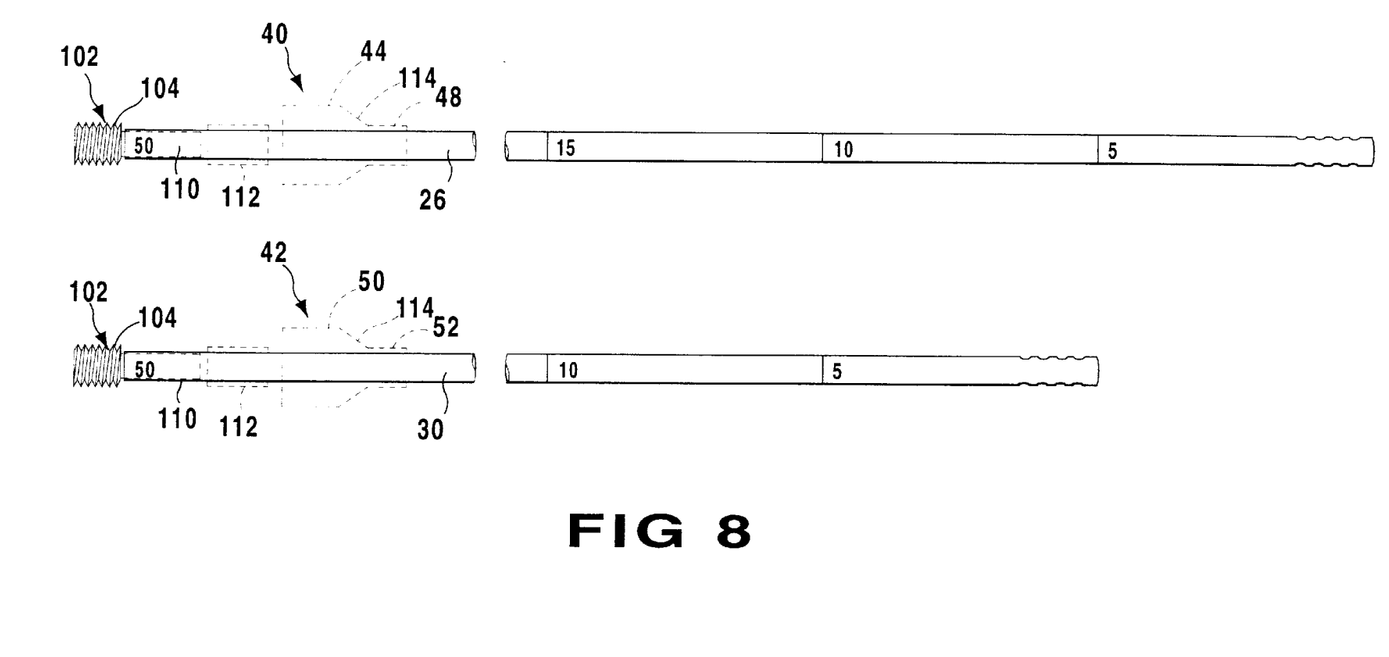
FIG. 8 is an exploded view of the end of the catheters of the implantable assembly for connecting a dialysis machine to a patient of the present invention.
Figure 9:
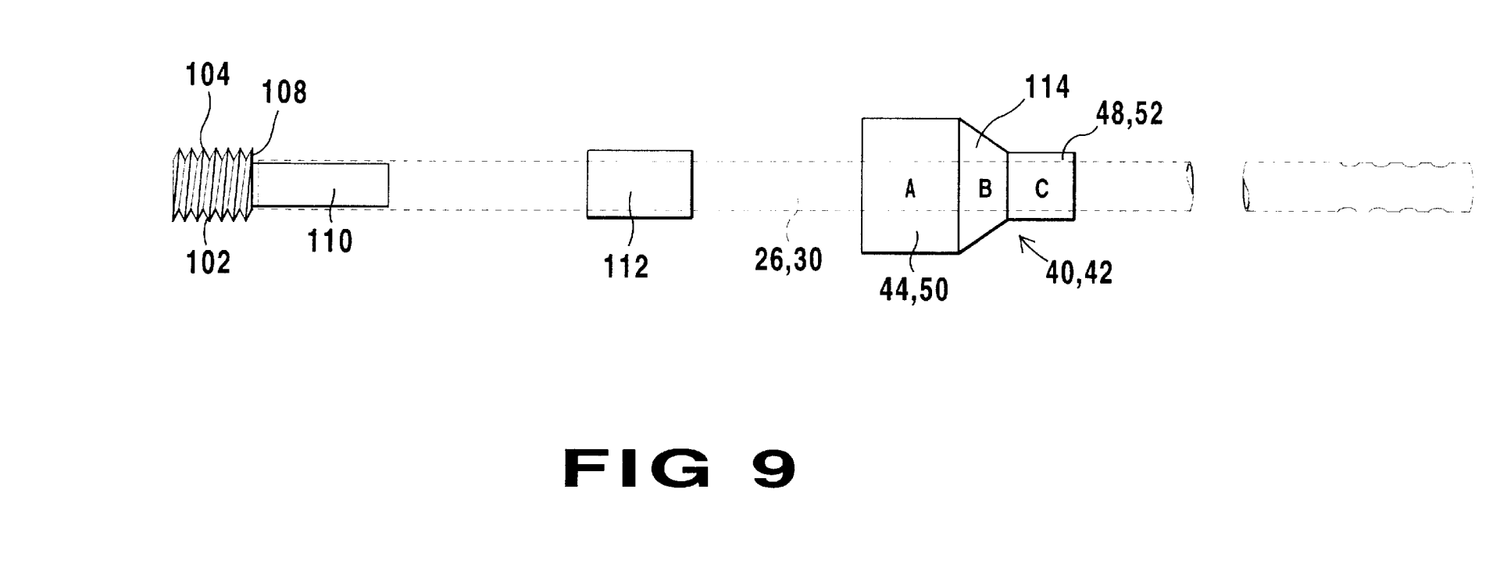
FIG. 9 is an exploded view of the end of the catheters of the implantable assembly for connecting a dialysis machine to a patient of the present invention.

FIGS. 8 and 9 illustrate an exploded view of the connection between the protrusion 102, connection port 40, 42 and catheter 26, 30. From these figures it can be seen that the catheter 26, 30 is extended through the connection port 40, 42 and positioned flush against a side 108 of the protrusion 102 with an extending portion of the protrusion forming an outlet catheter 110 positioned therein upon connection. A compression sleeve 112 is preferably positioned to surround the catheter 26, 30 between the catheter 26, 30 and the connection port 40, 42 forming a tight seal therebetween for preventing against leakage through the connection to the protrusion 102. The outlet catheter 110 is preferably formed of a metallic substance. The connection port 40, 42 is preferably formed of one of a plastic, Lucite, any polymeric material and any combination thereof. The compression sleeve 112 is preferably formed of silicone.

The protrusion 102 is hollow and preferably has an internal diameter of substantially 2.6 mm, an outer diameter of substantially 5.5 mm and a length of substantially 6 mm. The outlet catheter is also hollow and preferably has an internal diameter of substantially 2.0 mm, an outer diameter of substantially 2.6 mm and a length of substantially 10 mm. The compression sleeve 112 is hollow and preferably has an internal diameter of substantially 4.0 mm, an outer diameter of substantially 5.0 mm and a length of substantially 8 mm. The base section 44, 50 of the connection port 40, 42 preferably has an internal diameter of substantially 5.5 mm, an outer diameter of substantially 10 mm and a length of substantially 12 mm. The connection section 48, 52 of the connection port 40, 42 preferably has an internal diameter of substantially 4.0 mm, an outer diameter of substantially 5 mm and a length of substantially 4.0 mm. A mid section 114 of the connection port 40, 42 preferably has an internal diameter within a range of substantially 4.0 mm to substantially 5.5 mm, an outer diameter within a range of substantially 5 mm to substantially 10 mm and a length of substantially 3.0 mm. The catheter 26, 30 preferably has an internal diameter of substantially 2.5 mm, an outer diameter of substantially 3.9 mm and a length of substantially 50 cm.

The housing 13 is preferably substantially 2 cm thick and 8 cm wide at its widest point. The first and second recesses 54 and 56 preferably have a diameter of substantially 3 cm and the third recess 58 preferably has a diameter of 1.5 cm. The first, second and third recesses are preferably substantially 1.8 cm deep. The first and second ports 15 and 16 are preferably 1.2 cm thick and sit in the first and second recesses 54 and 56 forming a pool therebelow of a depth of substantially 0.6 cm. for receiving the blood passing therethrough. The third port 18 is preferably 0.6 cm thick and sits in the third recess such that a pool having a depth of substantially 1.2 cm is formed therebelow for receiving and storing heparin therein.

The first, second and third ports are lined with a suitably dense material for preventing the needle from piercing their walls and are formed from a self sealing material such as rubberized silicone for preventing the release of any fluids therefrom except through the needle inserted therein. The first and second ports are of a surface area of a size able to provide a large number of insertion points thereby allowing an area time to heal after puncture with the needle.

The operation of the implantable dialysis connection assembly 10 will now be described with reference to the figures. In operation, the implantable dialysis connection assembly 10 is prepared for implantation below subcutaneous tissue in a left subclavicular area of a patient 12. The first, second and third ports 15, 16 and 18 are positioned within their respective recess and the first and second catheters 26 and 30 are connected to the first and second connection ports 40 and 42 respectively. When the implantable dialysis connection assembly 10 is implanted in the body of the patient, the first and second catheters 26 and 30 are positioned to extend into the superior vena cava of the patient 12 and the securing devices 36 and 38 are sutured or stapled to the subcutaneous tissue in the left subclavicular area of the patient 12. The implantable dialysis connection assembly 10 is now secured within the body of the patient and ready for use. The implantable dialysis connection assembly 10 may be located by simply feeling around the area of implantation until located. The presence of the implantable dialysis connection assembly 10 is easily detectable.

When ready for use, the doctor will feel around the area of implantation to locate the three ports. Upon finding the first port 15, the first needle 76 connected to a first lead from the dialysis machine is inserted therein such that the first needle 76 extends through the first port and into the pool formed therebelow. When the second port 16 is located, the second needle 78 connected to a second lead from the dialysis machine is inserted therein such that the second needle 78 extends through the second port 16 and into the pool formed therebelow. Upon finding the third port 18, the third needle 80 connected to a heparin supply is inserted therein such that the third needle 80 extends through the third port and into the pool formed therebelow. As the size of the third port 18 is substantially smaller than the size of the first and second ports 15 and 16 it is easily distinguished therefrom thereby preventing accidentally connecting the heparin supply to either the first or second ports. The function of the first and second ports is interchangeable and thus distinguishing the first and second ports is not necessary.

Once the needles are inserted into their respective ports the patient is prepared to begin dialysis treatment. At this point the heparin is supplied through the third needle 80 and stored in the pool formed below the third port 18. The heparin supply will be drawn into the first and second recesses through the first and second conduits by osmosis. When the dialysis machine is turned on, blood is drawn through one of the catheters and into either the first or second port by a suction force exerted through one of the first and second needles. The blood drawn into the dialysis machine is detoxified and returned through the other of the first and second needles. The detoxified blood is then deposited in the pool in which the needle sits for mixing with the heparin drawn into the pool from the third port and return to the superior vena cava through the catheter connected thereto. As the operation of the first and second ports is interchangeable, blood may be drawn from or returned to the body through either of the first and second ports. The only condition being as the blood is drawn through one of the ports it is returned through the other. One port cannot perform both operations concurrently.

Once the blood of the patient is detoxified, the dialysis machine is turned off and the first, second and third needles are removed from their respective ports. As the first, second and third ports are formed of a sealable rubberized silicone material, the hole formed by the insertion of the needle is resealed once the needle is removed and thus the port is prepared for reuse. This also allows the port to be used a substantial number of times without the need for replacement thus increasing the life of the implantable dialysis connection assembly 10.

From the above description it can be seen that the implantable dialysis connection assembly 10 of the present invention is able to overcome the shortcomings of prior art devices by providing an implantable dialysis connection assembly 10 which is cosmetically appealing to the user and allows the user to assume a normal life style between dialysis treatments without the risk of epidermal infection normally associated with tubes providing external access to implanted catheters. The implantable assembly for connecting a dialysis machine to a patient includes identical arterial and venous ports which are easily locatable and discernible by application of light pressure to the skin with a hand and are accessible using right angle anti-coring needles attached to the dialysis machine and a third heparin port connected to both the arterial and venous ports for storing a supply of heparin therein and supplying the heparin to the arterial and venous ports for preventing the blood from clotting in the ports and thereby clogging the ports. The arterial and venous ports have a surface area of a size able to provide a large number of insertion points thereby allowing an area time to heal after puncture with the needle and are formed from a self sealing material such as rubberized silicone for preventing the release of any fluids therefrom except through the needle inserted therein. Each of the arterial, venous and heparin ports are also lined with a suitably dense material for preventing the needle from piercing the walls of the port. Furthermore, the implantable dialysis connection assembly 10 of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. An implantable dialysis connection assembly for connecting first and second catheters positioned with a vein in a patients body to first and second terminals of a dialysis machine, said implantable dialysis connection assembly comprising:

a) a housing including a face side, and first, second and third recesses extending into said face side;

b) a first port positioned within said first recess for receiving the first terminal and retaining an end of the first terminal within said first recess;

c) a second port positioned within said second recess for receiving the second terminal and retaining an end of the second terminal within said second recess;

d) a third port positioned within the third recess for connecting to a supply of heparin for deposit within the third recess;

e) a first conduit extending between said first and third recesses for supplying heparin from said third recess to said first recess;

f) a second conduit extending between said second recess and said third recess for supplying heparin from said third recess to said second recess;

g) first means extending from said first recess for connecting said first recess to the first catheter; and h) second means extending from said first recess for connecting said second recess to the second catheter, wherein blood is removed from the vein through the first catheter, said first connecting means and said first recess and through the first terminal retained within said first recess to the dialysis machine and blood is returned to the vein through the second terminal, said second recess, said second connecting means and the second catheter, said heparin being supplied to said first and second recesses during dialysis for preventing the blood passing through said first and second recesses from clotting and thereby clogging the first and second terminals.

2. The implantable dialysis connection assembly as recited in claim 1, wherein the first and second terminals each include a needle extending therefrom and said first and second ports each receive a needle of a respective one of the first and second terminals therein.

3. The implantable dialysis connection assembly as recited in claim 2, further comprising a first entrance extending between said first recess and said first means for connecting and a second entrance extending between said second recess and said second means for connecting.

4. The implantable dialysis connection assembly as recited in claim 3, further comprising a first hollow protrusion extending from said first entrance for connection to said first means for connection and a second hollow protrusion for connecting to said second means for connecting.

5. The implantable dialysis connection assembly as recited in claim 4, wherein said first protrusion includes a thread spiraling therearound and said first means for connecting is hollow and includes a thread spiraling around an inner side thereof for mating with said thread spiraling around said first protrusion.

6. The implantable dialysis connection assembly as recited in claim 5, wherein said second protrusion includes a thread spiraling therearound and said second means for connecting is hollow and includes a thread spiraling around an inner side thereof for mating with said thread spiraling around said second protrusion.

7. The implantable dialysis connection assembly as recited in claim 6, wherein the first catheter is secured within said inner side of said first means for connecting and the second catheter is secured within said inner side of said second means for connecting.

8. The implantable dialysis connection assembly as recited in claim 7, further comprising a first compression sleeve positioned between said inner side of said first means for connecting and the first catheter and a second compression sleeve positioned between said inner side of the second means for connecting and said second catheter.

9. The implantable dialysis connection assembly as recited in claim 8, wherein said first and second ports have a surface area of a size able to provide a large number of insertion points thereby allowing an area time to heal after puncture with a needle.

10. The implantable dialysis connection assembly as recited in claim 2, wherein said first and second ports each have a thickness and said first and second recesses each have a depth, said thickness of said first and second ports being less than the depth of said first and second recesses, respectively.

11. The implantable dialysis connection assembly as recited in claim 10, wherein a pool is formed in said first recess below said first port and a pool is formed in said second recess below said second port.

12. The implantable dialysis connection assembly as recited in claim 11, wherein said first and second ports are formed of a rubberized self sealing silicone material.

13. The implantable dialysis connection assembly as recited in claim 12, wherein said first and second ports each include a defining wall, said defining wall of said first and second ports being coated with a material able to prevent a needle inserted therein from piercing the defining wall.

14. The implantable dialysis connection assembly as recited in claim 13, wherein the needle extending from the first terminal extends through said first port and into said pool formed in said first recess upon insertion and the needle extending from the second terminal extends through said second port and into said pool formed in said second recess upon insertion.

15. The implantable dialysis connection assembly as recited in claim 1, wherein said assembly is implanted positioned below subcutaneous tissue in a left subclavicular area of the patient's body.

16. The implantable dialysis connection assembly as recited in claim 15, further comprising means extending from said housing for securing said assembly within the body of the user.

17. The implantable dialysis connection assembly in claim 16, wherein said means for securing is at least one of suchered and stapled to the subcutaneous tissue in the patient's body.

18. The implantable dialysis connection assembly as recited in claim 1, wherein said third port is formed of a rubberized self sealing silicone material.

19. The implantable dialysis connection assembly as recited in claim 1, further comprising means extending from said housing for securing said assembly within the body of the user.

* * * * *